(12) United States Patent
Boehm et al.

(10) Patent No.: US 9,907,629 B2
(45) Date of Patent: Mar. 6, 2018

(54) DENTAL PROSTHETIC ARRANGEMENT AND DENTAL PROSTHETIC SYSTEM

(71) Applicant: Bredent GmbH & Co. KG, Senden (DE)

(72) Inventors: Wilfried Boehm, Senden (DE); Peter Brehm, Senden (DE); Roland Benz, Ulm (DE)

(73) Assignee: Bredent GmbH & Co. KG, Senden (DE)

( * ) Notice: Subject to any disclaimer, the term of this patent is extended or adjusted under 35 U.S.C. 154(b) by 0 days.

(21) Appl. No.: 14/767,958

(22) PCT Filed: Feb. 5, 2014

(86) PCT No.: PCT/EP2014/052256
§ 371 (c)(1),
(2) Date: Aug. 14, 2015

(87) PCT Pub. No.: WO2014/124856
PCT Pub. Date: Aug. 21, 2014

(65) Prior Publication Data
US 2015/0351877 A1    Dec. 10, 2015

(30) Foreign Application Priority Data
Feb. 15, 2013   (DE) .......................... 10 2013 101 511

(51) Int. Cl.
*A61C 13/277* (2006.01)
*A61C 8/00* (2006.01)

(52) U.S. Cl.
CPC .......... *A61C 8/0054* (2013.01); *A61C 8/0057* (2013.01); *A61C 8/0062* (2013.01);
(Continued)

(58) Field of Classification Search
CPC ... A61C 8/0054; A61C 8/0057; A61C 8/0062; A61C 8/0069; A61C 8/0048;
(Continued)

(56) References Cited

U.S. PATENT DOCUMENTS 2,866,285 A * 12/1958 Gerber ............... A61C 13/2656
433/219
4,447,210 A *  5/1984 Hidaka ................ A61C 8/0086
433/169

(Continued)

FOREIGN PATENT DOCUMENTS

DE    10 2004 051 437 A1    6/2005
EP         0 894 480 A1    2/1999
(Continued)

OTHER PUBLICATIONS

International Search Report of PCT/EP2014/052256, dated Jun. 2, 2014.

*Primary Examiner* — Edward Moran
*Assistant Examiner* — Drew Folgmann
(74) *Attorney, Agent, or Firm* — Collard & Roe, P.C.

(57) ABSTRACT

A dental prosthetic arrangement and a dental prosthetic system include a combination of a lower part assigned to a jaw implant and an upper part assigned to a prosthesis body in a connection section, wherein in particular two bearing faces are produced in the connection section when in the connected state, the bearing faces being cylindrical, preferably circular-cylindrical in relation to a center axis and being spaced apart from each other in the axial direction. The axial extent of the cylindrical bearing faces is advantageously small compared to the axial extent of the connection section. The two cylindrical bearing faces are preferably situated in axially opposite end regions of the connection section and are connected to each other by approximately conical wall
(Continued)

faces of a cut-out in the upper part and a projection of the lower part that projects into the latter.

16 Claims, 3 Drawing Sheets

(52) U.S. Cl.
CPC .......... *A61C 8/0069* (2013.01); *A61C 13/277* (2013.01); *A61C 8/0048* (2013.01)

(58) Field of Classification Search
CPC ... A61C 8/0072; A61C 8/0086; A61C 8/0068; A61C 13/30; A61C 13/2656; A61C 13/225; A61C 8/005; A61C 8/0053
See application file for complete search history.

(56) References Cited

U.S. PATENT DOCUMENTS

| | | | | |
|---|---|---|---|---|
| 4,604,060 A * | 8/1986 | Weissman | .............. | A61C 13/30 433/221 |
| 4,850,873 A * | 7/1989 | Lazzara | .............. | A61C 8/0048 433/173 |
| 5,049,073 A * | 9/1991 | Lauks | .................. | A61C 8/0018 433/169 |
| 5,259,759 A * | 11/1993 | Jorneus | ................ | A61C 8/0048 433/173 |
| 5,344,318 A * | 9/1994 | Wilson | ................. | A61C 8/0048 433/169 |
| 5,439,381 A * | 8/1995 | Cohen | .................... | A61C 8/001 433/173 |
| 5,667,384 A | 9/1997 | Sutter et al. | | |
| 6,283,753 B1 * | 9/2001 | Willoughby | ......... | A61C 8/0001 433/172 |
| 6,299,447 B1 | 10/2001 | Zuest et al. | | |
| 6,716,030 B1 * | 4/2004 | Bulard | ................ | A61C 8/0048 433/174 |
| 2002/0177103 A1 * | 11/2002 | Pelak | ................... | A61C 8/0048 433/173 |
| 2010/0266985 A1 | 10/2010 | Yau et al. | | |
| 2012/0264082 A1 * | 10/2012 | Segura | ................ | A61C 8/0048 433/174 |
| 2014/0212842 A1 * | 7/2014 | Arnetzl | ............... | A61C 8/0066 433/173 |

FOREIGN PATENT DOCUMENTS

| | | |
|---|---|---|
| WO | 97/10770 A1 | 3/1997 |
| WO | 02/24104 A1 | 3/2002 |
| WO | 2012/065848 A1 | 5/2012 |

* cited by examiner

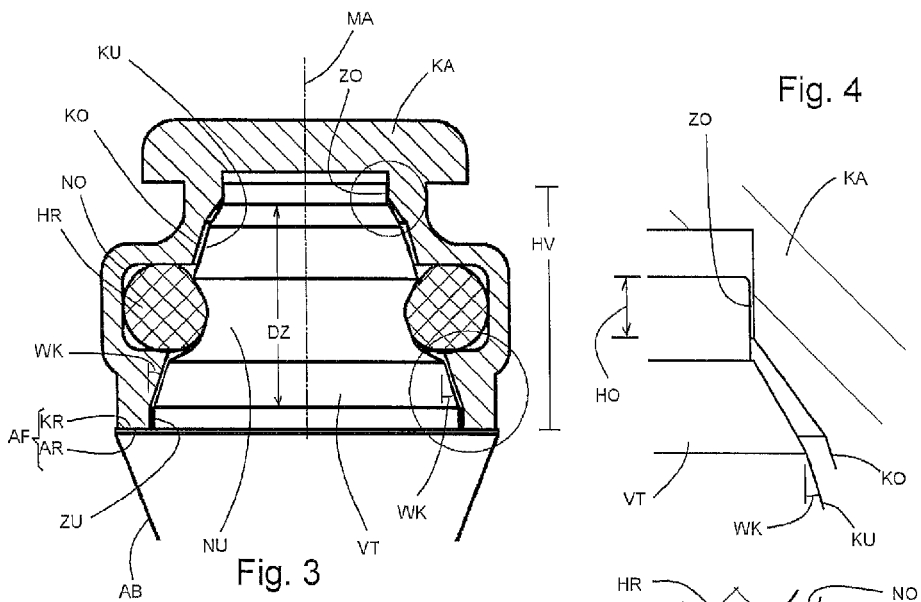
Fig. 4
Fig. 3
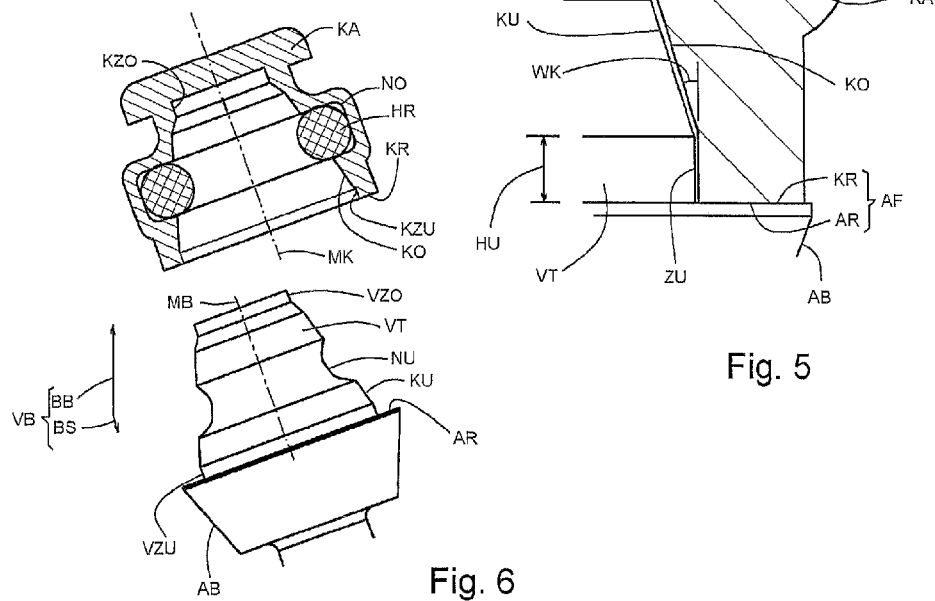
Fig. 5
Fig. 6

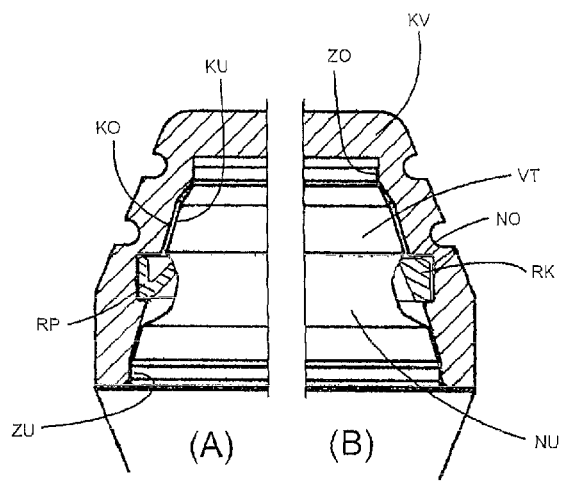
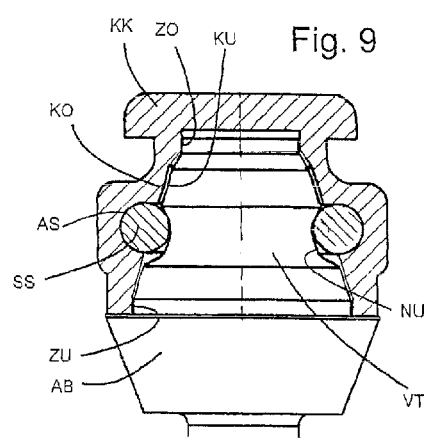
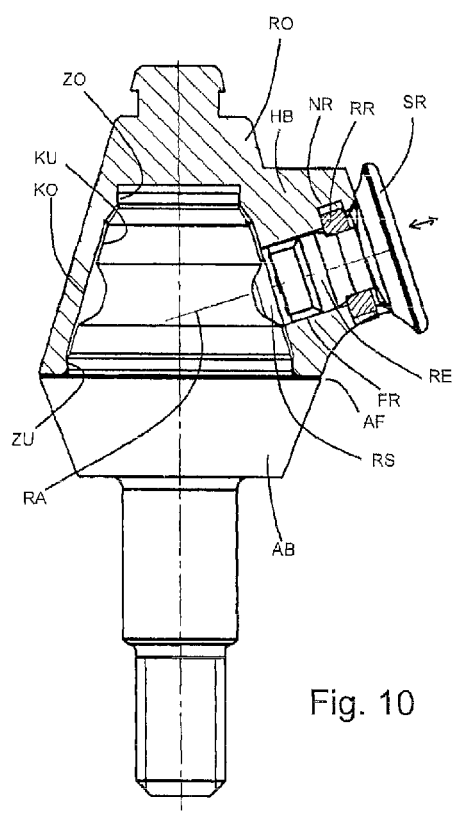
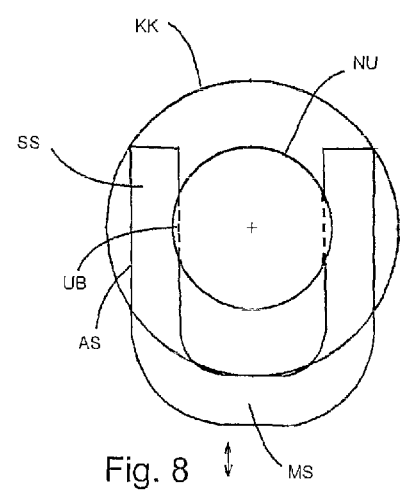
Fig. 7
Fig. 9
Fig. 8
Fig. 10

DENTAL PROSTHETIC ARRANGEMENT AND DENTAL PROSTHETIC SYSTEM

CROSS REFERENCE TO RELATED APPLICATIONS

This application is the National Stage of PCT/EP2014/052256 filed on Feb. 5, 2014, which claims priority under 35 U.S.C. § 119 of German Application No. 10 2013 101 511.5 filed on Feb. 15, 2013, the disclosure of which is incorporated by reference. The international application under PCT article 21(2) was not published in English.

BACKGROUND OF THE INVENTION

1. Field of the Invention

The invention relates to a dental-prosthetic assembly and to a dental-prosthetic system having such an assembly.

In dental prostheses for missing teeth, dental-prosthetic assemblies are increasingly being used, which have an abutment above a jaw implant anchored in the jaw bone. For the replacement of multiple adjacent teeth or even all the teeth of a jaw, a cohesive abutment can also be provided above multiple jaw implants, in advantageous manner.

2. Prior Art

The conventional manner of attaching a dental-prosthetic abutment to a jaw implant, by means of a cement, leads to a fixed tooth replacement. Cementing disadvantageously proves to be a cause for the by far predominant part of cases of peri-implantitis. Abutments that have been cemented on typically also cannot be removed in destruction-free manner.

In order to be able to remove the abutment without damage to or destruction of the implant, various systems of releasable attachment of a prosthesis to a substructure with one or more jaw implants are known. Typically, a prosthesis that can only be removed by a treating dentist, if necessary using a tool, is referred to as being removable with restrictions, and a prosthesis that can also be released and put into place by the wearer himself/herself, without tools, is referred to as being removable. Such prostheses, which are removable with restrictions or removable, at the same time avoid the aforementioned problems of cementing.

In U.S. Pat. No. 6,299,447 B1, a connection method in the manner of snaps is described, in which a cap that is open toward the jaw is cast into a prosthesis, and, on the jaw implant, a post widened in the manner of a bollard at the upper end, with a radial bulge, projects away from the jaw at the upper end. With the interposition of a ring having a radially convex-curved wall, the cap can be reversibly snapped onto the bollard and pulled off it, overcoming a holding force. Such assemblies are of particular advantage particularly for full prostheses, and can also be removed and re-inserted by the prosthesis wearer himself/herself, which is referred to as a removable prosthesis.

In U.S. Pat. No. 5,667,384, a dental-prosthetic assembly is described, in which a head screw is firmly screwed onto an implant. A recess in the cap of a removable prosthesis engages over the head screw, and an attachment screw that leads essentially radially through the cap supports itself on the screw head, at the bottom, with a conical surface, and presses the cap in the direction of the jaw implant, where prosthesis and implant are supported against one another at a conical sealing surface. The attachment screw simultaneously pulls the opposite inner wall laterally against the screw head. Instead of a head screw as part of a multi-part implant and as a counter-surface to the conical surface of the attachment screw, a sleeve attached to the jaw implant, having a conical outer wall, which forms a contact surface with a conical inner wall of the cap, and having a circumferential groove, can also form a counter-surface to the attachment screw. The prosthesis can be removed from the jaw by loosening the attachment screw in a medical practice; this is referred to as being removable with restrictions.

In DE 10 2004 051 437 A1, a double crown is described, in which a primary crown possesses a cylindrical outer surface and a secondary crown having a suitably formed recess can be pushed over the primary crown. The primary crown has a horizontal groove in its cylinder mantle surface, into which groove an elastic pin of the secondary crown engages and secures the secondary crown to prevent it from being pulled off the primary crown, with a holding force that must be overcome for pulling the primary crown off.

SUMMARY OF THE INVENTION

The present invention is based on the task of indicating an advantageous dental-prosthetic assembly having a prosthesis that can be attached in cement-free manner, particularly one that is reversibly removable or removable with restrictions, over one or more jaw implants, as well as a dental-prosthetic system having such an assembly.

Solutions according to the invention are described in the independent claims. The dependent claims contain advantageous embodiments and further developments of the invention.

In the dental-prosthetic assembly according to the invention, particularly advantageous force support occurs between the lower part assigned to the implant and the upper part assigned to the prosthesis, in the connection section, with simultaneously simple production and release of the connection. In this regard, the two cylindrical contact surfaces, which are axially spaced apart, for supporting the upper part against the lower part in the case of tilting moments that act due to external forces, are of particular importance. Preferably, the first and/or the second contact surface is/are configured to be circular-cylindrical.

In particular, multiple different holding elements can be provided in a dental-prosthetic system having such a dental-prosthetic assembly, which elements are designed differently, in such a manner that different holding elements bring about different holding forces in dental-prosthetic assemblies that are otherwise the same. The different holding elements can particularly differ with regard to their cross-section and/or material, for example elastomer material having different Shore hardness. Particularly in the case of the removable prostheses, a holding force appropriate for the respective user can then be set by means of selecting one of the multiple different holding elements.

The lower part can form a section of a one-part implant or one of multiple parts of a multi-part implant. In the case of multi-part implants, the lower part should be viewed as being firmly connected with the part of the implant anchored in the jaw bone, and as being non-displaceable in its position relative to the part anchored in the jaw, when setting the prosthesis into place and taking it off. The upper part is typically a part of a multi-part abutment of a prosthesis, and can particularly be structured as a cap cast into a prosthesis or as an abutment firmly connected with a prosthesis material.

The invention is based on the recognition that when using a prosthesis inserted into the mouth of a user, not only pressure force stresses but also tilting moments occur, which can be absorbed in particularly advantageous and reliable manner by means of the particular shape and orientation of contact surfaces, particularly of the first and second contact surfaces, which are cylindrical with reference to a center axis of the connection section, i.e. run parallel to the center axis in the axial direction and are spaced apart by a center section.

The first and/or the second, preferably both contact surfaces can preferably form circular-cylindrical ring surfaces having cylinder axes that run parallel, preferably align with one another, in an advantageous embodiment. The surfaces at which surfaces of upper part and lower part can touch each other, with force support, should be viewed as being contact surfaces. In this regard, upper part and lower part should stand opposite or touch one another essentially without play at the contact surfaces, so that when the force action on the prosthesis changes, no relative displacement of upper part to lower part that can be noticed by the user occurs. First and/or second contact surfaces can also be divided into partial surfaces that are separated from one another, for example if upper part or lower part have structures that do not have rotation symmetry or are interrupted in the circumference direction.

In a preferred embodiment, the connection section is completely covered, and the holding element that engages into the first structures of the projection of the lower part and the second structures of the recess of the upper part is inaccessible and protected. In this regard, the holding element is preferably configured as a ring. In another advantageous embodiment, the holding element can also be accessible to the user or, in particular, to a treating dentist, in the case of an upper part connected with the lower part, and can be activated manually or by means of a tool. In this regard, the holding element can particularly be configured as a latch element that can be displaced transverse to the center axis and relative to upper part and lower part, between a holding position with engagement into first and second structures, and a release position in which at least the engagement into the first structures is cancelled out, for example as a pivot latch or preferably as an insertion latch, also in pin form or bracket form. In general, an extra-coronal holding element, support element or connection element for partial prostheses as well as for supra-constructions of implants can be understood to be a latch element.

Because of the axial distance between first and second contact surface and the lesser diameter of the second cylindrical contact surface, as compared with the diameter of the first cylindrical contact surface, a movement direction of the upper part relative to the lower part is required only during a short axial movement path, and the remainder of the movement path can deviate from this axial direction.

The cone angle of an imaginary truncated cone between first and second contact surfaces advantageously amounts to at least 10°. Preferably, this cone angle amounts to maximally 20°. In the center section of the connection section, the outer wall of the lower part assigned to the implant and the inner wall of the upper part assigned to the prosthesis preferably run at least approximately in the form of a truncated cone that narrows away from the implant. Upper part and lower part are spaced apart from one another by a slight dimension in the center section, and are not directly supported on one another, with transfer of force. The conicity of the connection section is particularly advantageous with an orientation of the center axis of the connection section that is inclined (angled) against the occlusion plane.

BRIEF DESCRIPTION OF THE DRAWING

The invention is exemplified in greater detail below, using preferred exemplary embodiments and making reference to the figures. These show.

DETAILED DESCRIPTION OF THE PREFERRED EMBODIMENTS

Figures 1, 2:
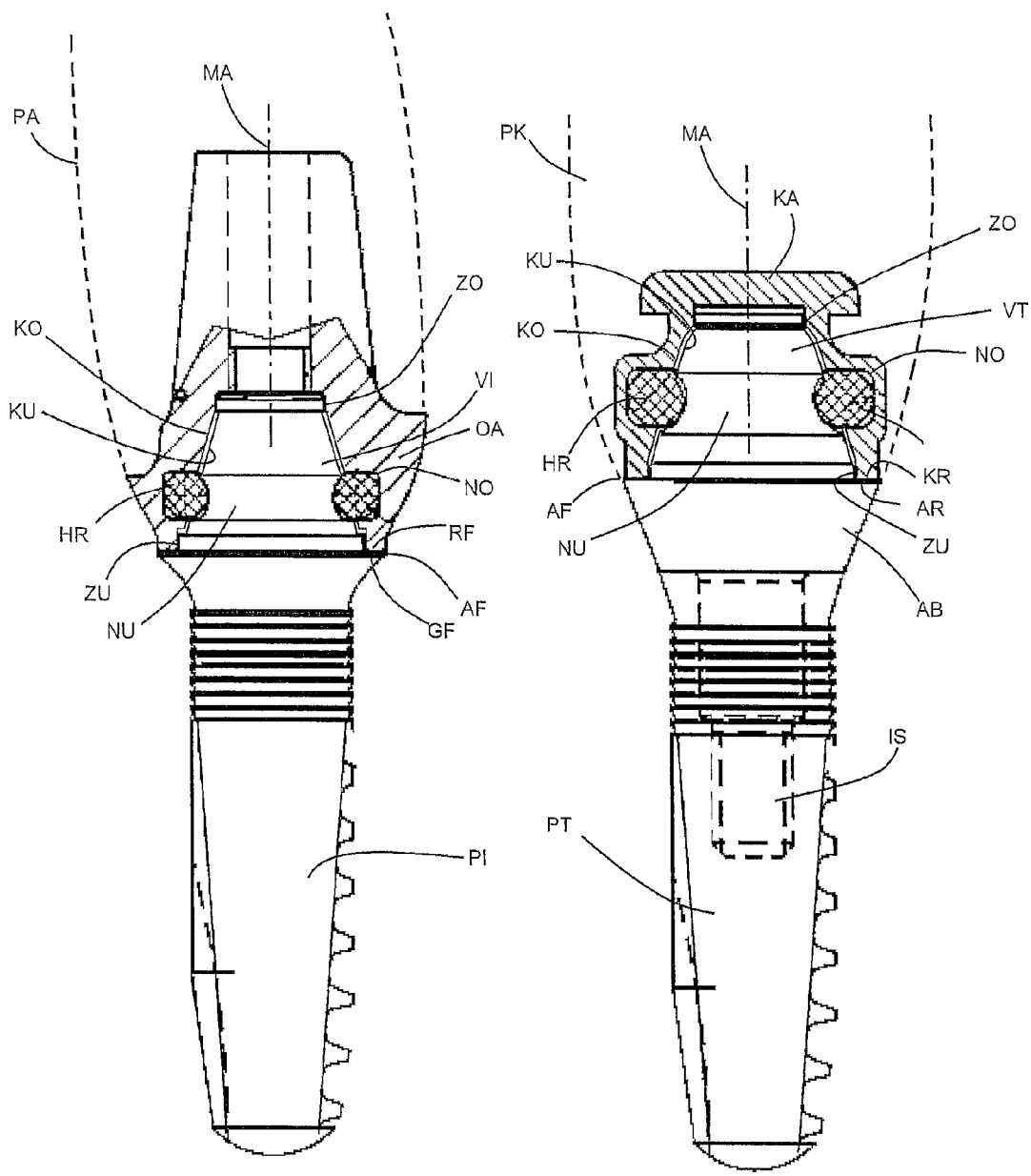
FIG. 1 a first assembly according to the invention,
FIG. 2 a second assembly according to the invention,
FIG. 3 an enlarged representation of a connection section,
FIG. 4 an enlarged detail of an upper cylinder surface,
FIG. 5 an enlarged detail of a lower cylinder surface,
FIG. 6 an assembly representation,
FIG. 7 variants of ring cross-sections,
FIG. 8 a top view of a variant having an inserted bracket,
FIG. 9 a side view of FIG. 8,
FIG. 10 a variant having a latch.

FIG. 1 shows a first embodiment of a dental-prosthetic assembly according to the invention in a side view, partly in section, in which assembly a prosthesis PA is attached to a one-part jaw implant PI. A projection VI projects away from the one-part jaw implant PI, at its end facing away from the jaw, which projection possesses an approximately conical lateral mantle surface KU. This projection VI forms a lower part of a connection section between the abutment of the prosthesis body PA and the jaw implant PI. The projection VI projects into a recess of an abutment body OA of the prosthesis, which body forms an upper part of the connection section. The lateral inner wall of the abutment body OA advantageously forms an approximately conical surface KU, wherein the conical mantle surface KO of the lower part and the conical inner wall KO of the upper art do not, however, touch one another in the joined state shown.

A groove NU that is recessed toward a center axis MA of the connection section is introduced into the essentially conical mantle surface KU of the lower part VI; a groove NO that is recessed away from the center axis MA, in the approximately conical inner wall surface KO of the abutment body OA of the upper part lies radially opposite the former groove NU in the joined state of upper part and lower part. A holding ring HR as a holding element engages into both grooves NU, NO, and brings about a holding force that counteracts the upper part from being pulled off the lower part in the direction of the center axis MA.

The abutment body OA as an upper part of the connection section is supported on the projection VI that forms the lower part of the connection section, at multiple contact surfaces. In this regard, a ring-shaped base surface GF that faces away from the jaw-side end of the implant, in the direction of the center axis, is still considered part of the lower part of the connection section. A ring surface RF on the face end of the abutment body OA, facing the implant, is supported on the base surface GF of the lower part in the direction of the center axis, and reliably absorbs the axis-parallel components of force components that act on the upper part OA, by way of the prosthesis body PA, parallel to the center axis MA.

Such support for absorbing force components parallel to the center axis MA is actually known.

The abutment body OA as the upper part of the connection section is furthermore supported against the lower part, in the radial direction with reference to the center axis MA, by means of a lower cylindrical contact surface ZU and by means of an upper cylindrical contact surface ZO. The abutment body OA and the lower part VI lie against one another essentially without play at the lower cylindrical contact surface ZU that forms a first contact surface and at the upper cylindrical contact surface ZO that forms a second contact surface.

In FIG. 2, a variant of a dental-prosthetic assembly is shown, in which a jaw implant is structured in two parts, with a first part PT anchored in the jaw bone and an abutment AB attached to the former by means of a screw connection IS and secured to prevent rotation. In this embodiment, the abutment AB forms the lower part of the connection section with a projection VT approximately in the shape of a truncated cone, facing away from the jaw-side end of the implant.

A cap KA is set onto the projection VT as part of a prosthesis body PK, as the upper part of the part of the prosthesis body that forms the connection section. The cap KA can particularly be cast into prosthesis material of the prosthesis body PK, and is firmly and permanently anchored in the prosthesis body PK, for which reason the outside of the cap KA has structures for shape-fit anchoring in the prosthesis body PK.

The projection VT, as part of the abutment AB, should once again have an at least approximately conical outer wall KO, which stands opposite an also approximately conical inner wall surface KU of the cap KA in the joined-together state shown in FIG. 1, at a slight radial distance.

In analogy to the embodiment according to FIG. 1, a surface AR enclosing the projection VT in ring shape, corresponding to the surface GF of the implant according to FIG. 1, is formed on the abutment AB, on which surface a ring-shaped face surface KR of the cap KA, corresponding to the surface RF according to FIG. 1, lies against, to absorb vertical pressure forces between upper part and lower part of the connection section, and once again to form a ring-shaped contact surface AF. The ring-shaped contact surfaces AF according to FIG. 1 and FIG. 2 are preferably planar ring surfaces with a surface normal line parallel to the center axis MA.

In the approximately conical mantle surface KU of the projection VT that forms the lower part, once again a circumferential ring groove NU is formed, which stands radially opposite a ring groove NO in the approximately conical inner wall surface KO of the cap KA. A holding ring HR engages into both ring grooves NU, NO and brings about a holding force between upper part and lower part, to prevent removal in a direction parallel to the center axis MA.

Also in a manner analogous to FIG. 1, a first contact surface in the form of a contact surface ZU that is cylindrical with reference to the center axis MA is formed at the lower end of the projection VT, which faces the jaw-side end of the implant, on which surface ZU cylindrical wall surface sections of projection VT and cap KA stand opposite one another, essentially without play, or touch one another. In corresponding manner, a second contact surface in the form of an upper cylindrical contact surface ZO is formed at the end of the connection section that faces away from the jaw-side end of the implant, between the projection VT and the cap KA.

FIG. 3 shows the connection section of the assembly according to FIG. 2 in an enlarged representation, from which, enlarged once again, the region of the second contact surface, as an upper cylindrical contact surface ZO is shown in FIG. 4, and the region of the first contact surface, in the form of the lower cylindrical contact surface ZU, is shown in FIG. 5.

The direction information above and below makes reference, in this regard, to the representation in the figures, which reproduce the approximate position of the dental-prosthetic assembly when the jaw implant is anchored or is to be anchored in the lower jaw. When the jaw implant is anchored in the upper jaw, the direction information is reversed correspondingly, to the extent that this information refers to the wearer of the prosthesis.

In FIG. 3, it is expressed more clearly, by means of the enlargement, that the conical wall surfaces KO of the cap KA and KU of the projection VT, approximately in the form of a truncated cone, are spaced apart from one another by a narrow gap, so that no transfer of forces takes place between cap KA as the upper part and projection VT or abutment AB as the lower part, by way of contact of the conical wall surfaces KU, KO, and the individual force components between cap KA and abutment AB are transferred exclusively by way of the upper cylindrical contact surface ZO, the lower cylindrical contact surface ZU, as well as the surface AF, which is preferably planar and ring-shaped.

The holding ring HR, which preferably consists of an elastically deformable material, can advantageously bring about a basic force as a press-down force parallel to the center axis, at the ring-shaped contact surface AF, even in the absence of external forces that act on a prosthesis body above the upper part KA, in that the holder ring HR is biased by means of elastic deformation, in the position shown in FIG. 3, in such a manner that it brings about a basic force on the contact surface AF.

In this regard, the grooves NO and NU are offset from one another in the axial direction of the center axis MA in the exemplary embodiment according to FIG. 3, so that the ring HR generates an axial bias, with elastic deformation. In particular, the ring supports itself axially, in this regard, on an upper section of the groove NU and a lower section of the groove NO.

FIG. 6 shows an abutment AB and a cap KA in a state in which they are released from one another, before the upper part is set onto the lower part or after the upper part has been taken off the lower part. In this regard, let it be assumed that the entire prosthetic assembly comprises multiple jaw implants and a cohesive prosthesis body that contains multiple caps KA. The jaw implants can be anchored in the jaw with an inclined orientation, and thereby different conditions in the jaw bone can be taken into consideration, depending on the patient, in each instance. Such an inclined orientation can have the result that by means of one or more connection sections, at which caps KA are connected with implants, a movement sequence VB when removing the prosthesis body and setting it into place is primarily determined by the structure of the prosthesis body, and does not coincide with the direction of the center axis MK of the cap KA and of the center axis MB of the implant or abutment AB that aligns with it in the assembled state.

In the structure of the connection section according to the invention, with the first and second contact surfaces, which are cylindrical with reference to the center axis MA, as well as the lesser diameter of the second cylindrical contact surface ZO, use is made, in particularly advantageous manner, of the fact that in spite of a deviation of an inclined center axis MA of the connection section according to FIG. 3 that might be present, or of center axis MK of the cap KA and center axis MB of the projection VT according to FIG. 6, as compared with a connection direction predetermined by the prosthesis body, in accordance with a movement section BB in FIG. 6, the prosthesis body is elastically resilient to such an extent that a movement part BS of a total movement process VB is possible, even parallel to the center axis MA or the center axes MK, MB, over a short movement section. In this short movement section BS, engagement at the two cylindrical contact surfaces ZU, ZO, with precise fit, is produced or released. By means of the lesser diameter of the second contact surface as the upper cylindrical contact surface ZO as compared with the diameter of the lower cylindrical contact surface ZU, a cap KA of the prosthesis body can be displaced relative to the implant, after release of or before production of the engagement at the two cylindrical contact surfaces, with precise fit, without contours of the recess in the cap or contours of the projection of the lower part reciprocally interfering with one another.

At the same time, when engagement of upper part and lower part, with precise fit, exists at the first and second contact surface as the lower and upper cylindrical contact surface, precise positioning transverse to the center axis MA as well as reliable force support exist.

In FIG. 6, the different contact surfaces of the cap KA as the upper part and of the projection VT as part of the abutment as the lower part, on the other hand, are still indicated individually. A first, lower inner wall surface KZU, which is cylindrical with reference to the center axis MK of the cap KA, forms the cylindrical lower contact surface ZU with a first, lower wall surface VZU, which is cylindrical with reference to the center axis MB of the abutment, in the joined state. An upper cylindrical wall surface KZO of the cap KA forms the second cylindrical contact surface ZO, with an upper cylindrical mantle surface VZO of the projection VT, in the joined state. The cylindrical surfaces KZO, KZU, VZO, and VZU are preferably configured to be circular-cylindrical.

The dimension of the axial overlap of the cylindrical wall surfaces KZO, VZO, with the formation of the upper cylindrical contact surface ZO, is indicated as HO in FIG. 4. In corresponding manner, the dimension of the axial overlap of the cylindrical wall surfaces KZU and VZU, with the formation of the lower cylindrical contact surface ZU, is indicated as HU in FIG. 5. The engagement depths or the axial expanses HO, HU of the cylindrical contact surfaces ZO, ZU are advantageously significantly smaller than the axial expanse of the connection section indicated as HV in FIG. 3, which section is measured, in this regard, from the contact surface AF all the way to the upper edge of the second cylindrical contact surface ZO. It is advantageous if the engagement depths HO, HU are also significantly smaller than the axial distance DZ between the cylindrical wall surfaces within the lower part or within the upper part.

A cone angle of the at least approximately conical wall surface KU of the lower part is indicated in FIG. 3 with WK, as the angle of inclination of a mantle line of the surface KU relative to the center axis MA. The value of such a cone angle WK advantageously amounts to more than 10°, particularly more than 12°. It is advantageous if the cone angle is less than 20°, particularly less than 18°.

The engagement depths HO, HU of the two cylindrical contact surfaces advantageously amount to at least 0.1 mm, preferably at least 0.2 mm. To take the movement process when placing a prosthesis body onto implants and/or removing it, as described, into consideration, the engagement depths HO, HU advantageously do not amount to more than 0.4 mm. The axial expanse HV of the connection section is typically on the order of between 2.5 mm and 6 mm. The axial length of the first and/or of the second cylindrical contact surface advantageously amounts to less than 20%, particularly less than 15%, and preferably more than 5% of the axial expanse HV of the connection section. In this way, tilting when joining or releasing upper part and lower part can be avoided, to a great extent, in spite of a low gap width of advantageously less than 0.03 mm, particularly less than 0.02 mm at the upper and/or lower cylindrical contact surfaces. The outside diameter of the ring-shaped further contact surface AF typically lies on the order of from 3 mm to 5 mm, preferably approximately 4 mm.

The holding ring HR, which lies in the grooves NO and NU in the jointed state and brings about the holding force to prevent removal, as a holding element, can particularly consist of a plastic, which should be understood to also include an elastomer or a rubber material. Preferably, the groove NO in the upper part has a greater radial depth relative to the approximately conical surface KO than the groove NU relative to the conical surface KU. The holding ring HR then advantageously lies in the groove NO of the upper part in the state of the dental-prosthetic assembly with the upper part released from the lower part, as shown in FIG. 6, and can thereby be replaced outside of the mouth of the prosthesis wearer, if necessary, for example in order to be able to insert a new holder ring in the case of wear of the holding ring HR after multiple reversible placement and release of the prosthesis body onto or from the implants, or in order to carry out a comparison with different holding rings, to try out a holding force that is appropriate for the user, one after the other.

The holding force brought about by the holding ring HR in the preceding examples can be designed not only in a range for a removable prosthesis with frequent placement and removal by the user himself/herself, but also for a prosthesis that is removable with restrictions, which typically has a higher holding force.

The holding ring HR can also be configured for a permanent connection of upper part and lower part, by means of designing its string cross-section and/or material in connection with the cross-sections of the grooves NU, NO, for which purpose it can also be provided that although the connection can be released in a dental practice, the holding ring might be destroyed in the process.

In FIG. 7, two variants of non-round string cross-sections of holding rings are shown, wherein a variant of a holding ring RP shown in the left half of FIG. 7, as FIG. 7(A), has a V-shaped string cross-section with two shanks, which are elastically pressed toward one another when the upper part KV is set onto the lower part VT, and are automatically pressed apart again when the groove NU is reached. Release of the connection of the upper part KV from the lower part VT has the result, in this variant, that removal can take place only with greater force and typically with destruction of the holding ring RP. The string cross-section of the holding ring RP, as shown, does not need to remain the same over the entire circumference, but rather can also be present only at multiple circumference sections.

A further variant, shown in FIG. 7 (B), shows a wedge-shaped string cross-section of a holding ring RK, in which a wedge tip is disposed facing away from the jaw-side end of the implant, and in this way, an increased holding force to prevent the upper part KV from being pulled off the lower part VT exists. Depending on the configuration of the string cross-section and the selection of the material of the holding ring RK in detail, lifting the upper part KV off the lower part VT can take place with destruction of the ring RK or while maintaining it.

The string cross-sections of the holding rings RP and RK shown in FIG. 7 bring about an asymmetry of the forces between placement of the upper part KV onto the lower part VT and pulling the upper part KV off the lower part VT, in the direction of the center axis MA, in particularly advantageous manner.

FIG. 8 schematically shows an embodiment, with a viewing direction along the center axis MA, in which a U-shaped holding bracket, particularly a wire bracket having lateral bracket shanks SS that run tangentially with reference to the center axis MA and at a radial distance from it, and a center section MS of the U-shaped bracket that connects the two side shanks, is provided. The bracket is preferably displaceable in the direction of the double arrow shown in FIG. 8, between a holding position and a release position, manually or by means of a tool. The lateral bracket shanks SS can be shaped in deviation from the straight form shown, in order to lie against the groove NU, which is shown, in FIG. 8, as a circular line of its upper delimitation, with elastic bias, and to thereby prevent unintentional slipping out of engagement. A recess AS that runs transverse to the center axis MA is provided for the bracket in the upper part, for example in the form of tangential bores or a ring groove having additional wall perforations. FIG. 9 shows an example of an assembly according to FIG. 8 in a view partly in section, with a viewing direction perpendicular to the center axis MA and parallel to the direction of the side shanks SS of the U-shaped bracket according to FIG. 8. The side shanks SS lie in openings AS of a cap KK, wherein the openings AS are open, at least in certain sections, toward the approximately cone-shaped inner wall KO of the cap KK. Bracket shanks SS of the bracket that lie in the openings AS then lie partly in the openings AS with their cross-section and partly in the groove NU of the projection VT of the lower part, and prevent the upper part KK from being pulled off the lower part VT.

In the embodiment shown in FIG. 8, lifting the upper part KK off the lower part VT is only possible if the U-shaped bracket is previously displaced out of the openings AS of the upper part KK, in the direction of the arrow shown in FIG. 8, until the lateral bracket shanks SS are displaced out of engagement with the groove NU in the overlap regions that are indicated with UB in FIG. 8. The wire diameter of a wire used as a bracket can advantageously amount to approximately 0.6 mm to 1 mm.

A further variant of holding an upper part RO on a lower part VT as part of an abutment AB is shown in FIG. 10. In this connection, a form of the lower part as in FIG. 2 to FIG. 9 should be assumed. The upper part RO has a holding region HB, radially continued with reference to the center axis, in which region a latch assembly is configured. In this regard, a latch element RE can be displaced in a latch accommodation FR oriented predominantly radially with reference to the center axis MA, in the direction of a latch axis RA, between an engagement position shown in FIG. 10, and a release position that is displaced away from the center axis MA in the direction of the latch axis RA. The latch element RE engages into the groove NU of the lower part VT with a latch top RS, and in this engagement position prevents the upper part RO from being lifted off the lower part VT. The latch element RE is pressed in the direction of the center axis MA, setting up a spring force, and thereby maintains the engagement position on its own. The spring force is applied, in the advantageous example shown, in that an elastically deformable ring RR lies in a groove NR that surrounds the latch axis RA in the holding region HB, which ring is supported against displacement in the direction of the latch axis RA in the groove NR and interacts with a cone surface that narrows away from the latch tip RS, over the course of the latch element RE, in such a manner that a force on the latch element in the direction toward the center axis MA occurs. The ring RR can consist of elastic plastic material or also be formed by a metal ring, which can also be slit. A handle. SR disposed outside of the latch guide FR allows manual retraction of the latch element RE from the engagement position shown in FIG. 10, and afterward lifting of the upper part from the lower part. In this connection, the ring RR can be compressed by means of the said cone surface of the latch element and by increasing the force on the latch element that acts as a reset force, or can be radially widened into a free space within the groove NR.

In place of the plug-in latch shown in FIG. 10, other latch elements that can be displaced transverse to the center axis, particularly pivot latches, pins, etc. can be provided.

The characteristics indicated above and in the claims, as well as those that can be derived from the figures, can be advantageously implemented not only individually but also in different combinations. The invention is not restricted to the exemplary embodiments described, but rather can be modified in many ways, within the scope of the ability of a person skilled in the art.

The invention claimed is:

1. A dental-prosthetic assembly comprising a jaw implant and an abutment, which are connected with one another in a connection section, by way of a lower part assigned to the jaw implant and an upper part assigned to the abutment, wherein, in the connection section, the lower part engages into a recess of the upper part with a projection that surrounds a center axis of the dental-prosthetic assembly, the lower part and the upper part are supported against one another at multiple contact surfaces, with transfer of force, a first contact surface is a first cylindrical contact surface, coaxial to the center axis, at an end of the connection section closest to the jaw implant, a second contact surface is a second cylindrical contact surface, coaxial to the center axis, at an end of the connection section farthest from the jaw implant, a diameter of the second contact surface is less than a diameter of the first contact surface, a third contact surface is formed by a ring-shaped surface at the end of the connection section closest to the jaw implant, the ring-shaped surface being planar, wherein the upper part has a conical wall surface, and the projection has approximately the shape of a truncated cone, the projection comprising a projection conical wall surface corresponding to the conical wall surface of the upper part, wherein force components between the upper part and the lower part can be transferred exclusively by way of the first contact surface, the second contact surface, as well as the third contact surface, wherein in a center section, a holding element engages into a first structure of the projection and a second structure of the recess, and brings about a holding force to prevent the upper part from being axially pulled off the lower part, wherein the conical wall surface and the projection conical wall surface extend both below and above the holding element, wherein the conical wall surface and the projection conical wall surface are spaced apart from one another by a first narrow gap and a second narrow gap, so that no transfer of forces takes place between the upper part and the lower part by way of contact of the conical wall surface and the projection conical wall surface, wherein the first narrow gap is disposed above the holding element, and wherein the second narrow gap is disposed below the holding element.

2. The dental-prosthetic assembly according to claim 1, wherein the holding element lies against the first structure and the second structure in a rest state, free of external forces, under elastic bias, and brings about an axial press-down force against the third contact surface under the elastic bias.

3. The dental-prosthetic assembly according to claim 1, wherein a cone angle of the projection conical wall surface of the lower part or a cone angle of the conical wall surface of the upper part in a region between the first contact surface and the second contact surface lies between 10° and 20°.

4. The dental-prosthetic assembly according to claim 1, wherein the first structure is formed by a ring groove.

5. The dental-prosthetic assembly according to claim 1, wherein the second structure is formed by a ring groove.

6. The dental-prosthetic assembly according to claim 1, wherein the holding element contains at least one latch element that can be displaced transverse to the center axis.

7. The dental-prosthetic assembly according to claim 1, wherein the holding element is formed by an elastically deformable ring.

8. The dental-prosthetic assembly according to claim 7, wherein the elastically deformable ring comprises a rubber-elastic and/or elastically compressible material.

9. The dental-prosthetic assembly according to claim 1, wherein the second structure has at least one insertion opening.

10. The dental-prosthetic assembly according to claim 9, wherein the holding element has at least one pin-shaped section.

11. The dental-prosthetic assembly according to claim 1, wherein the second structure has a perforation that is directed radially with reference to the center axis.

12. The dental-prosthetic assembly according to claim 11, wherein the holding element can be radially displaced in the perforation.

13. The dental-prosthetic assembly according to claim 1, wherein the holding force can be overcome without destruction of the upper part and the lower part, in order to release the connection between the upper part and the lower part.

14. The dental-prosthetic assembly according to claim 1, wherein the holding force can be overcome without destruction of the holding element.

15. The dental-prosthetic assembly according to claim 1, wherein the upper part and the lower part can be connected with elastic deformation of the holding element, with an axial plug-in movement.

16. A dental-prosthetic system comprising:
a dental-prosthetic assembly according to claim 1, and
at least one additional holding element interchangeable with the holding element of the dental-prosthetic assembly,
wherein the at least one additional holding element and the holding element are for different holding forces.

* * * * *